United States Patent [19]

Shilo et al.

[11] Patent Number: 4,894,161
[45] Date of Patent: Jan. 16, 1990

[54] PROCESS FOR CLARIFYING A LIQUID USING A POLYMERIC SUBSTANCE

[75] Inventors: Moshe Shilo, Jerusalem; Ali Fattom, Maale Hagalil, both of Israel

[73] Assignee: Solmat systems, Ltd., Yavne, Israel

[21] Appl. No.: 927,947

[22] Filed: Nov. 7, 1986

Related U.S. Application Data

[60] Division of Ser. No. 634,535, Jul. 26, 1984, Pat. No. 4,649,110, which is a continuation of Ser. No. 403,047, Jul. 29, 1982, abandoned.

[51] Int. Cl.[4] ................................................ C02F 1/54
[52] U.S. Cl. ..................................... 210/602; 47/1.4; 210/611; 210/725; 210/728; 210/730; 435/946
[58] Field of Search .................... 47/1.4; 210/602, 611, 210/730, 725, 728; 435/68, 101, 257, 84, 946

[56] References Cited

U.S. PATENT DOCUMENTS

| | | |
|---|---|---|
| 2,732,661 | 1/1956 | Spoehr et al. . |
| 2,908,113 | 10/1959 | Martin . |
| 3,208,526 | 9/1965 | Patton et al. . |
| 3,346,463 | 10/1967 | Goren .................................... 195/31 |
| 3,374,081 | 3/1968 | Miller . |
| 3,396,104 | 8/1968 | Miller .................................. 210/725 |
| 3,406,114 | 10/1968 | Goren .................................. 210/730 |
| 3,432,427 | 3/1969 | Moore .................................... 210/4 |
| 3,462,360 | 8/1969 | McKinney ........................... 210/730 |
| 3,493,499 | 2/1970 | Zeitoun ................................ 210/727 |
| 3,598,730 | 8/1971 | Nordgren et al. ................... 210/730 |
| 3,681,283 | 8/1972 | Yueh .................................... 210/730 |
| 3,684,706 | 8/1972 | Bomstein ............................. 210/730 |
| 3,732,089 | 5/1973 | Megronigle ............................ 71/8 |
| 3,763,039 | 10/1973 | Wilson ................................. 210/730 |
| 3,820,281 | 6/1974 | Bigler et al. .......................... 47/1.4 |
| 3,850,799 | 11/1974 | Ludwig . |
| 3,889,418 | 6/1975 | Porter et al. .......................... 47/1.4 |
| 3,958,364 | 5/1976 | Schenck et al. . |
| 4,078,331 | 3/1978 | Savins et al. ......................... 47/1.4 |
| 4,078,332 | 3/1978 | Savins ................................... 47/1.4 |
| 4,079,544 | 3/1978 | Savins ................................... 47/1.4 |
| 4,087,936 | 5/1978 | Savins et al. ......................... 47/1.4 |
| 4,235,043 | 11/1980 | Harasawa et al. . |
| 4,236,349 | 12/1980 | Ramus . |
| 4,253,271 | 3/1981 | Raymond . |
| 4,320,594 | 3/1982 | Raymond ............................. 47/1.4 |
| 4,341,038 | 7/1982 | Block et al. . |
| 4,417,415 | 11/1983 | Cysewski et al. .................... 47/1.4 |
| 4,456,532 | 6/1984 | Leslie et al. ......................... 210/907 |

OTHER PUBLICATIONS

Avimelech et al., Science, vol. 216, Apr. 2, 1982, pp. 63–65.
Research Thesis by R. Zur, entitled Interaction Between Algal And Inorganic Suspended Solids, M. Sc. Thesis, 7/1979.

Primary Examiner—Peter Hruskoci
Attorney, Agent, or Firm—Sandler & Greenblum

[57] ABSTRACT

J-1 which is a strain of cyanobacteria is used to form and excrete a material useful as a flocculating agent and as an additive useful in soil conditioning. Method of separating and culturing the cyanobacteria under conditions necessary to achieve maximum formation and excretion of the material into solution. Method of purifying and separating excreted as well as intracellular material from cyanobacterial. Method of clarifying a particulate-laden liquid with a material excreted by cyanobacteria, and particularly species J-1. Extracellular polymeric material which is water-soluble, non-dialyzable, having a molecular weight greater than 100,000, based on Sephadex column elution G 150, containing sugar, peptide, and fatty acid moieties, giving a positive Anthrone test, having an absorption peak of 205 nm. using a Perkin-Elmer spectrophotometer Model 402.

17 Claims, 4 Drawing Sheets

Procedure of Bioflocculant Seperations

PROCESS FOR CLARIFYING A LIQUID USING A POLYMERIC SUBSTANCE

This is a division of application Ser. No. 634,535 filed July 26, 1984 now U.S. Pat. No. 4,649,110, which is a continuation under 1.60 of application Ser. No. 403,047, filed July 29, 1982 now abandoned.

BACKGROUND OF THE INVENTION

1. Field of the Invention

The invention relates to a method of separating bacteria from a liquid and to a method for culturing the bacteria to produce a polymer useful in liquid clarification and soil conditioning. The invention further relates to the polymeric substance produced and to methods of using the polymeric substance.

2. Description of the Prior Art

Industries which use large amounts of water or other liquids have in many cases been confronted with the problem of purifying these liquids of suspended particulate matter. Where time is not a critical factor, these undesirable particulates may settle out by themselves to the bottom of a container holding the liquid. However, in many cases the particulate matter will not settle out, even after long periods of time.

One of the best solutions to this problem in the past has been the addition of various inorganic chemical flocculants which cause the particulates to adhere to one another and to settle out. The problem with suspended particles is that they are in a colloidal suspension, in which the particles usually have a negative electrical charge. Hence, these particles repel one another and do not coalesce readily to form particles which are sufficiently large to precipitate. The flocculation process involves the neutralization of the charge on the particles. However, neutralization is only the first step. Stirring of the water causes collisions of the small neutralized particles, and forms a so-called "microfloc". Further growth of particles then occurs to form particles of sufficient size to settle rapidly in a sedimentation basin.

In the past, the most widely used flocculating agents have been various ferric salts and alum. More recently, various types of organic polymers have gained wide acceptance as flocculants. Though somewhat more expensive than the traditional inorganic flocculants, the greater effectiveness of organic polymers usually more than offsets the price differential. Furthermore, the older method of using inorganic polymers required relatively large amounts of inorganic salts. This practice added not only to the costs of the chemicals but also to the costs associated with the handling and the disposal of large volumes of sludge.

The above-mentioned polymeric materials do not occur naturally, thus, potential users must purchase the materials, at considerable cost, from various chemical manufacturers.

It would, therefore, be desirable to use as flocculants polymer materials which could be readily and inexpensively produced or secured.

SUMMARY OF THE INVENTION

It is an object of the invention to provide a process for the production of novel bioflocculants and the use of these bioflocculants in water clarification and in soil conditioning.

The object of the invention is achieved through the use of cellular excretions of a benthic filamentous cyanobacteria of the Phormidium genus in the family Oscillatoriacleae. This strain has been found to exist in a portion of the Jordan river where it was noticed that the water seemed to be clarifed of its particulates. The species of the invention has been denominated as J-1. J-1, is, in effect, a definite strain of an undefined species of the Phormidium genus. A specimen of this organism is being deposited with the American Type Culture Collection in Rockville, Md. This strain has a regeneration time of 24–48 hours and under the carefully controlled conditions of the invention the organism excretes a polymeric material which is useful to achieve the objectives of the invention.

The organisms of the invention are found naturally in fresh water. These organisms can be removed from the water for culturing according to an inventive technique by adding non-polar hydrocarbons into the water containing the bacteria and agitating the water to disperse the hydrocarbon into globules. Because benthic bacteria (including members of the Phormidium genus) are hydrophobic the bacteria become attached to the dispersed globules of hydrocarbon. The hydrocarbon is collected as it floats to the water surface, and the bacteria can then be separated from the hydrocarbon and grown under laboratory conditions.

The hydrocarbon treatment can also be used to remove the bacteria from a liquid body where the bacteria are being grown in situ, when, for various reasons, the liquid body (e.g., a solar pond) is being treated in some other manner that requires the removal of the bacteria, or when it is desired to secure samples of the bacteria for testing and for use elsewhere.

Once the hydrocarbons have been separated according to the inventive technique, the separated cyanobacteria are ready for treatment according to another aspect of the invention. Under specially controlled and tailored growth conditions, in properly selected media, and under defined physiological conditions, the cyanobacteria of the invention can be made to produce and excrete effective amounts of a polymeric substance useful as a flocculent as well as in fulfilling other purposes and objectives as set forth above. According to the invention the bacteria are made to produce the bioflocculant towards the end of an exponential growth phase and to excrete an active, high-molecular-weight substance into the external milieu during a dormant phase, which substance is extremely active as a bioflocculant.

For the exponential growth phase to occur, the microorganisms must be provided with an adequate amount of light. The temperature should range between 27°–33° C. The mineral requirements of the organisms are preferrably met by using a Chu-11 medium.

The extracellular substance is water-soluble, non-dialyzable, and has a molecular weight greater than 100,000, based on Sephadex column elution G 150. It contains sugar, peptide and fatty acid moieties, gives a positive Anthrone test and has an absorption peak at 205 nm using a Perkin-Elmer spectrophotometer Model number 402. The motility in the Spehadex columns appears to indicate that the inventive composition is a single substance, although this has not as yet been conclusively established.

The bacteria, whether separated or not, is subjected to the careful growth conditions so as to produce effective concentrations of the polymer. The bacteria is first subjected to conditions necessary to achieve an exponential growth condition. This treatment is continued for approximately six days until the bacteria begins to produce increased levels of the polymer towards the end of the six day period. Exponential growth is then stopped and the bacteria are made to enter a dormant phase by reducing calcium ion concentrations in the solution. During this phase effective levels of the polymer are excreted into the surrounding solution.

Although the entire crude bacteria containing solution may then be used as a bioflocculant, according to one embodiment of the invention the polymeric bioflocclant may be separated from the remainder of the solution. The separation may be performed by centrifuging or by passing the solution over a glass filter. The pellet (or filtrate) is then agitated to break open the cells, and if desired, proteins can be broken down with Protease. The polymer can then be precipitated with ethanol. The supernatant of the original solution which contains suspended polymer can be evaporated and then contacted with chloroform. The polymer concentrates itself at the chloroform aqueous interface which is then separated and evaporated. The polymer is then again precipitated by ethanol addition.

Although the above technique is cell destructive, the invention likewise includes techniques in which only the original supernatant is treated to remove bioflocculant while the cell containing pellet is reused by being subjected to an exponential growth phase.

When small quantities of about 0.5 mg per liter of the inventive bioflocculant are added to turbid fluids, it is found that suspended bentonite particles, which would otherwise remain in stable suspension, are rapidly sedimented (in ten minutes or less). The bioflocculant is also found to be effective in sedimenting suspended dust and organic particulates as well as clay suspensions. Lower doses of the bioflocculant, on the order of about 0.05 mg per liter, also show precipitating activity, but require longer periods on the order of several hours. The bioflocculant material is useful in treating even very high concentrations of particulates.

Through the use of the excreted polymeric material of the invention, large scale precipitation of clay suspensions can be achieved thus facilitating clarification of highly turbid water in canals, irrigation ditches, solar ponds, and other water bodies.

To achieve effective flocculation of particulate suspensions the liquid must have a minimum cation concentration. However, this cationic concentration is generally present in virtually all liquids to be treated.

In one embodiment of the invention, the bioflocculant can be added to ponds and reservoirs in crude culture concentrate form to facilitate particle removal.

According to another embodiment of the invention, special ponds can be constructed, containing either fresh or brackish water, which contain the Phormidium bacteria. Although J-1 is limited to NaCl concentrations of less than 1% other closely related bacteria may be used which are less salt sensitive. These ponds can be adjacent to the water bodies to be treated such that continuous or batch addition of the bioflocculant material to the water body can be easily achieved by adding liquid containing the bacteria to the body of liquid to be treated. In these special ponds mass cultivation of bioflocculant producing species J-1 of Phormidium can be conducted under conditions suitable for optimal production of the flocculant substance. The bioflocculant material can also be produced in situ in some cases by culturing the bacteria in the very liquid to be treated.

The naturally-occurring bioflocculant material may also be used to treat industrial waste water, particularly water contaminated with metal ions or radioactive minerals. Furthermore, the bioflocculant of the invention can also be used in conjunction in intensive closed system fish breeding systems, sewage systems, cooling towers, and other types of water purification equipment.

It is to be understood that the inventive bioflocculant is useful for the treatment of nonaqueous liquids as well, and that such treatment is considered to be within the scope of the invention.

In addition to its uses in the purification of water bodies and other liquids, the bioflocculant of the invention may be used to treat or condition soil by improving the colloidal properties of the soil and its water absorption capacity. In such a case it could be conveniently added to the soil via irrigation water. The soil to be treated could be greenhouse soil as well as outdoor soil, and soil used in plant nurseries and for growth of edible mushrooms.

BRIEF DESCRIPTION OF THE DRAWINGS

The above objects, features and advantages of the present invention will be more fully apparent to those of ordinary skill in the art to which this invention pertains from the following detailed description when considered in connection with the accompanying drawings, wherein.

DETAILED DESCRIPTION

Figure 1:
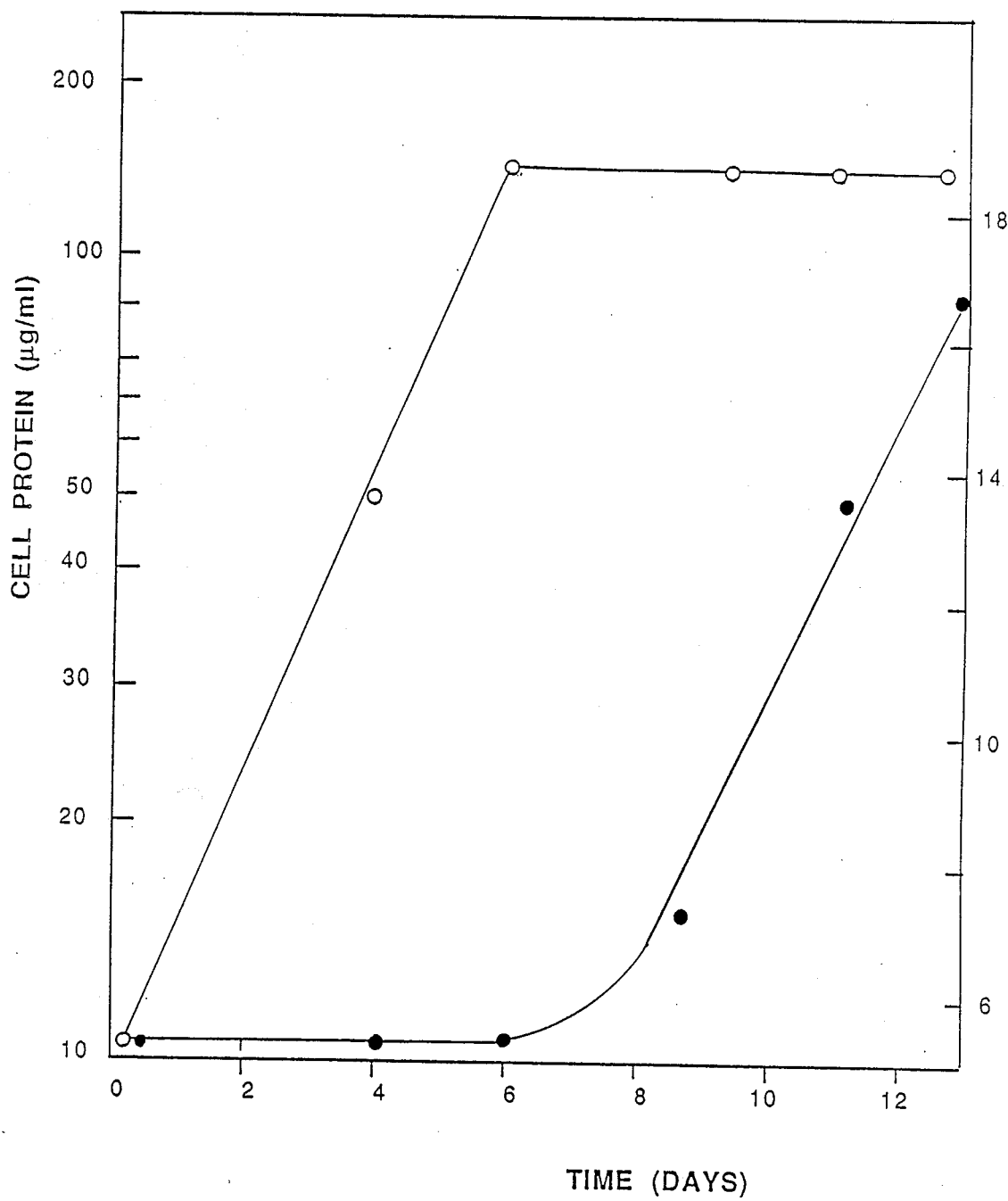
FIG. 1 is a graph of bioflocculant production, plotting the time in days (abscissa) against the cell protein content (in micrograms per milliliter) of Phormidium (left ordinate) and the amount of bioflocculant excreted (in micrograms per milliliter) (right ordinate)

The bacteria of the invention have been found in nature and may be cultured either in the laboratory or in their natural environment to produce the inventive compositions. Alternatively, the bacteria may be transplanted from growth in other bodies of water.

When it is desired to obtain a concentrated sample of the inventive bacteria from its environment in bodies of water the bacteria are separated from their natural environment and then may be cultured under controlled conditions. Separation may be performed by means of a filtration or by liquid-liquid separation techniques.

According to a liquid-liquid separation technique of the invention one or more non-polar water immiscible hydrocarbons such as xylene, heptane, octane, hexadecane and mixtures thereof, is added to the bacteria-containing body of water and agitated to form globules. By virtue of the non-polar nature of the hydrocarbons benthic bacteria (including some members of the Phormidium species, particularly J-1) will have a tendency to be absorbed into the hydrocarbon globules by virtue of their hydrophobic nature. By dispersing the hydrocarbon into small globules, improved separation is achieved. This occurs by virtue of the improved liquid-liquid contact providing a greater effective globule surface area. Depending upon the nature of the environment, various agitation and/or mixing techniques may be used to accomplish this purpose.

After sufficient agitation, the hydrocarbon material with J-1 adhering thereto is separated from the liquid. Standard two-phase liquid separation techniques may be used for this purpose. Thus, for example, the hydrocarbon globules, such as heptane, may be collected by centrifugation or filtration and then separated. The bacteria is then separated from the heptane phase by any one of a standard number of techniques. For example, small scale separation may be achieved by filtration of the bacteria cells on glass microfiber filters. On a large scale other filtration techniques may be used.

It should be noted that other hydrophobic bacteria, other than species J-1, which may be present in the original liquid environment may also unavoidably be removed by means of the liquid-liquid separation technique referred to above when the bacteria are found in an uncontrolled non-laboratory environment. When this is the case the J-1 species is preferably separated from the undesired bacteria when a pure culture is desired.

Once the bacteria have been collected, and are in a medium where variables can be controlled, the bacteria may then be conditioned so as to produce effective amounts and concentrations of the desired bioflocculant material.

The bioflocculant is preferably prepared in the following manner:

Cyanobacteria of the Phormidium genus (strain J-1) do not ordinarily produce sufficient quantities of the desired bioflocculant. The production of sufficient amounts of the bioflocculant is dependent on the physiological state of the organism. To achieve sufficient production, the organism must be allowed to proceed from a relatively dormant phase through an exponential growth phase. During this exponential growth phase the proper nutrients must be readily available. The nutrients are preferrably provided by using a Chu-11 medium. Essential materials include nitrogen and phosphate as well as light and carbon dioxide from the atmosphere. Also required are adequate light and a temperature range between about 27°-33° C.

As may be seen from FIG. 1, the exponential growth phase requires about 6 days during which time cell protein increases to about 140 micrograms/ml. Late, towards the end of the exponential growth phase, the cells begin to form increased concentrations of the inventive material extracellularly. The exponential growth phase is then at least partially arrested, e.g., by means of calcium ion deprivation (see FIG. 1).

By limiting the amounts of available calcium in the solution approximately 17 micrograms of flocculant per milliliter of solution at the above concentration of Phormidium cell protein (see FIG. 1) is excreted into the solution. This excretion occurs over a period of approximately 7 days. This amount is far in excess of what would be produced if calcium had not been cut off.

Calcium deprivation may be achieved either by limiting the amount of calcium added to, or present in the solution containing the microorganism, or by adding a chelating agent such as EDTA which, when added in sufficient amounts may similarly increase biofocculant excretion ten-fold by reducing the effective available concentration of calcium ions.

The solution containing the microrganism and bioflocculent may then be treated to separate and concentrate the bioflocculant material. As was noted above, this was not always necessary, since, in certain cases, it may be desirable to simply add the solution containing both microorganisms and bioflocculent to the liquid being treated. However, when desired, the invention provides a technique for separating and concentrating bioflocculent from a solution which contains the microorganism and bioflocculent.

According to the technique, the solution containing the cell culture is first centrifuged for 10 minutes at a velocity of 10,000 RPM with a centrifugal force of 6500 g, so as to result in a pellet and supernatant. Although FIG. 4 refers to centrifugation, it is to be understood that filtration could likewise be used, in which case solids would be trapped on the filter, with the purified liquid corresponding to the supernatant shown in FIG. 4. For purposes of the following discussion the term "pellet" will be used. However it is understood that this term likewise includes filtrates when a filtration technique is contemplated.

The pellet is then resuspended in distilled water thus forming a solution of microorganism cells which contain bioflocculant material intracellularly in combination with a certain amount of extracellular bioflocculant which may not have been separated as a result of the centrifugation or filtration steps. In order to remove intracellular bioflocculant, glass beads are added to the solution, and the solution is then agitated to break the cells. The resulting solution is then filtered on a glass fiber filter (GF/C furnished by Whatman) and is buffered with tris-hydroxymethyl-aminomethan (Serva Feinbiochemica). $MgSO_4$ is then added to a final concentration of 10 mg/ml. The solution is then incubated with Protease at a concentration of 100 micrograms/ml. at 37° C. for 60 minutes to break down proteins in the solution. It is to be understood that this step is optional where protein does not interfere with the ultimate bioflocculant activity contemplated. Finally, the solution is incubated with a 2:1 V/V ethanol solution for 60 minutes at 0° C. As a result of this incubation, a precipitate containing the bioflocculant is formed and the supernatant may be either discarded, or recycled or used in some other manner.

Figure 4:
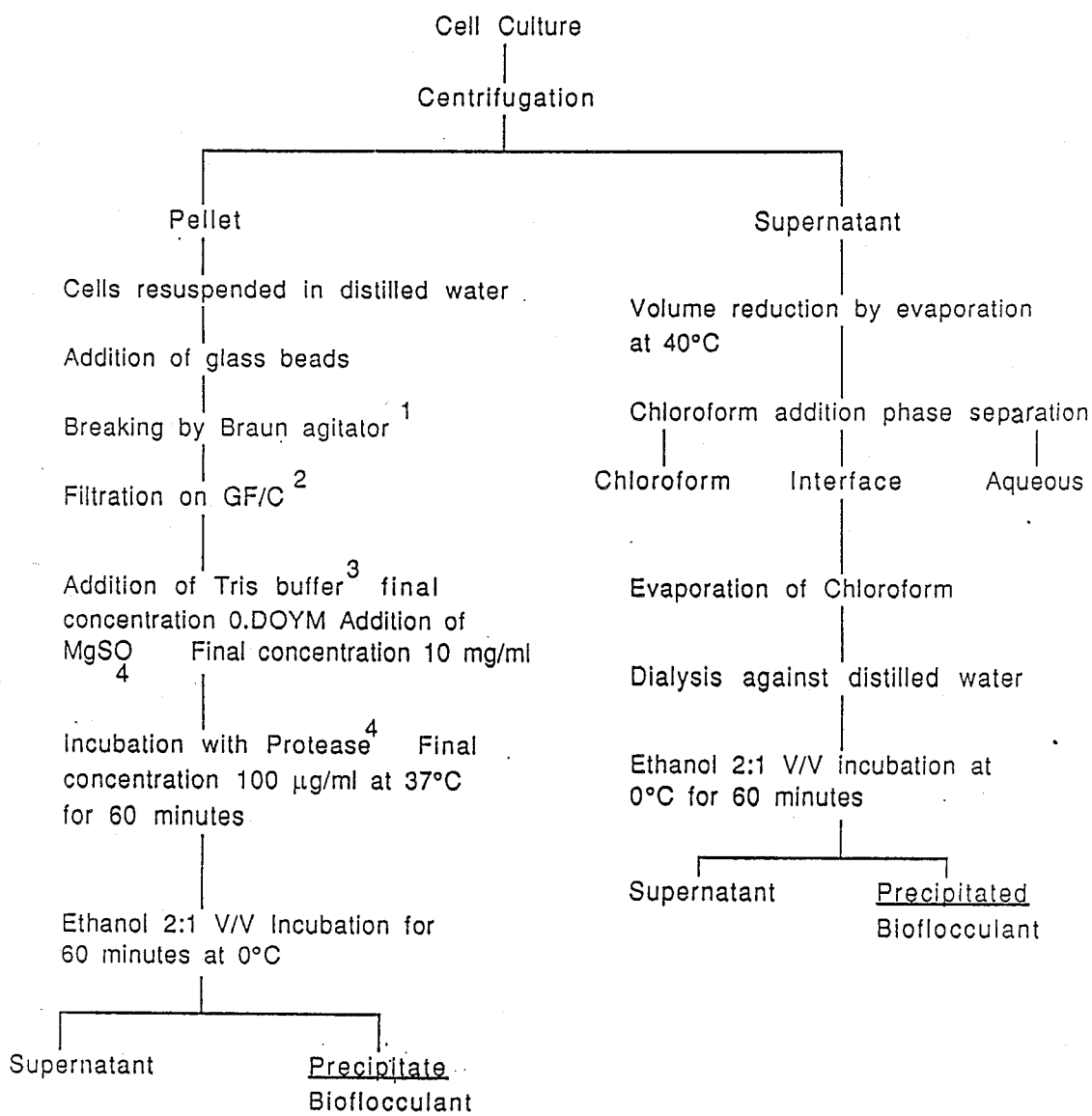
FIG. 4 is a flow chart for the separation and purification of bioflocculant from a solution.

The supernatant resulting from the original centrifugation or filtration of the cell culture which contains the bioflocculant material is treated as shown in FIG. 4, by evaporation or any other volume reduction technique so as to concentrate the supernatant. The concentrated supernatant is then contacted in a liquid-liquid contact system so as to form a two phase chloroform-aqueous system. It has been found that the bioflocculant material concentrates at the chloroform-aqueous interface. Thus, removing the liquid in the interface region removes the operating bioflocculant from the remainder of the system. The interface liquid is then evaporated to remove choloform and then dialyzed against distilled water. Finally, the dialyzed solution is incubated at 0° C. for 60 minutes in a 2:1 V/V ethanol solution to form a bioflocculant precipitate and a supernatant which may be recycled, discarded or used in any other manner.

Clearly, the treatment of the pellet as described above is cell destructive, and requires that a fresh batch of microorganism be provided if the bioflocculant production is to be repeated. Thus, where it is desired that the microorganisms be reused, the cells clearly should not be destroyed, and can be taken from the dormant phase and then reconditioned by proper treatment to once again undergo exponential growth whereby the process can be repeated. It should additionally be noted that the technique illustrated in FIG. 4 provides a method for removing any intracellular bioflocculant remaining within the microorganisms. Although it is preferable to first subject the microorganisms containing increased levels of bioflocculant to a dormant phase which results in a excretion of the bioflocculant, if, for some reason, it is not desired to subject the microorganisms to the dormant phase, the cells containing increased levels of bioflocculant may simply be destroyed to recover intracellular bioflocculant, thus obviating the dormant phase of the conditioning process.

The polymeric material of the invention is found to be a cell-free substance which is water-soluble, and non-dialyzable. Its molecular weight is greater than 100,000 (based on Sephadex column elution G 150). The substance is a polymer known to contain sugar, fatty acid and peptide moieties. It gives a positive Anthrone test and has an absorption peak at 205 nm on a Perkin-Elmer spectrophotometer Model 402.

If desired, the bioflocculant thus prepared can be directly added to the water or other liquid to be purified. When flocculating bentonite, minimal concentrations of a cation are preferably added, although such materials are generally present in the required concentrations in most bodies of water which would normally be treated. The preferred concentration of bioflocculant depends on the cation. For $Mg^{++}$, a minimum concentration of 0.001 gr %, for $Ca^{++}$, 0.003 gr %, and for $Na+$, 0.009 gr % are preferred. Mixtures of the cations may also be used. $Mg++$ ion addition is most preferred for purposes of the invention.

Figure 3:
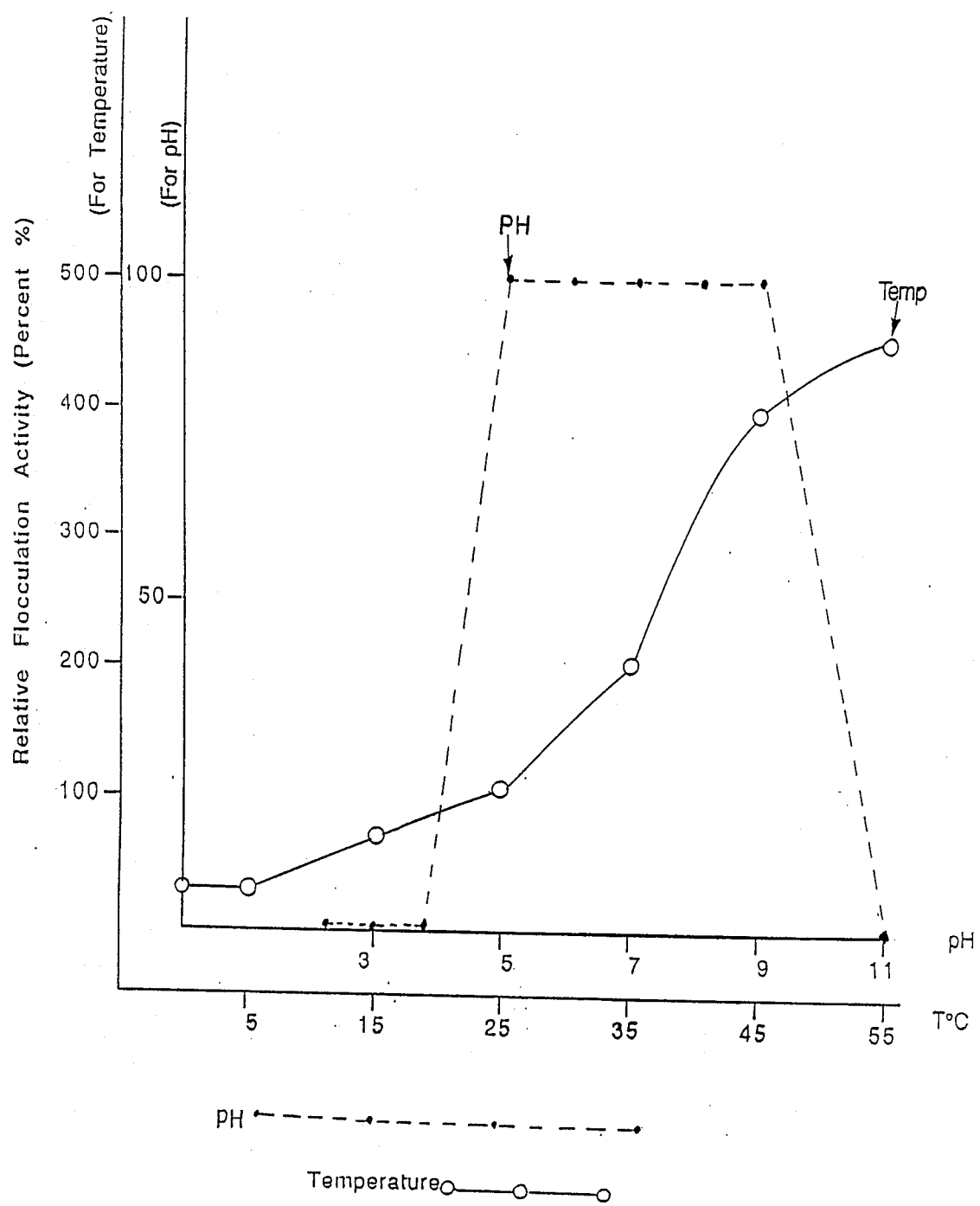
FIG. 3 is a graph illustrating the relative flocculating activity as a function of pH and temperature of the medium in which flocculation occurs.

As seen from FIG. 3, flocculating activity is steadily enhanced by increasing temperature within the range of from about 5° C. to about 55° C. and the flocculation may be performed in a temperature range of about 10°-80° C.

Flocculation activity is measured by preparing a standard suspension of bentonite, and then measuring the extent of bentonite flocculation by measuring optical density after 5 minutes at 25° C.

The bioflocculant is effective over a wide range of pH values, and may preferably be used at a pH value of anywhere from about 4.0 to about 11.0. Again, flocculating activity is pH dependant and, as may be seen from FIG. 3, flocculation is most effective at a pH range of about 5-9.

Figure 2:
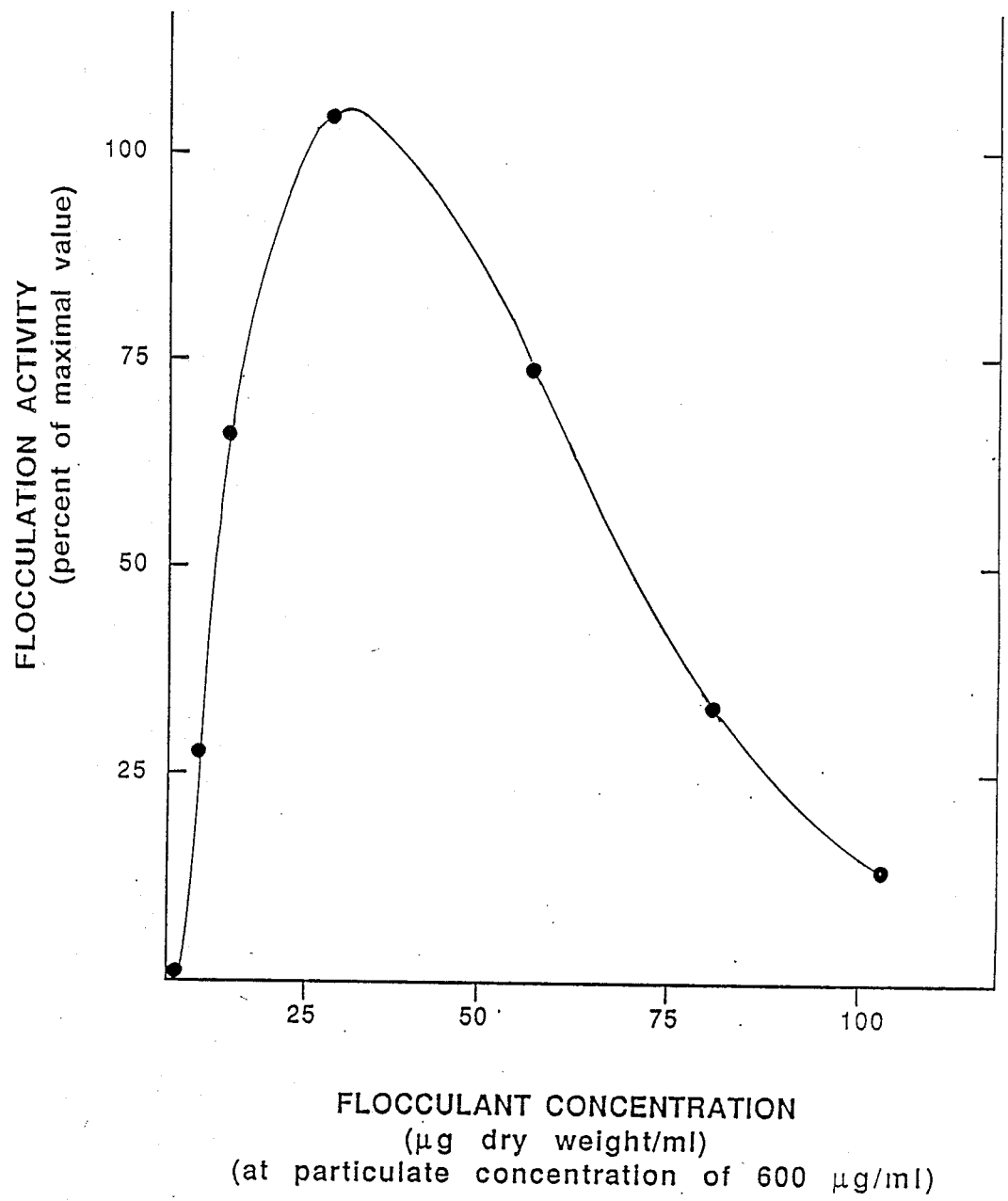
FIG. 2 is a graph plotting flocculant concentration (abscissa) against flocculant activity as a percentage of maximal value (ordinate); and flocculant concentration

The activity level of the bioflocculant is dose-dependent (see FIG. 2). There is a clear optimum precipitation concentration. As seen from FIG. 2, at an excess flocculant concentration, little, if any, flocculation is obtained. There is thus an optimum concentration at which flocculation activity reaches a peak which may be determined for each particular system. In certain systems water clarity can be critical, such as in salt water solar ponds which function at maximum efficiency only when the sun's rays can penetrate far into the pond. The clearer the water, the farther the sun's rays will be able to travel, thus increasing the efficiency of the solar pond.

According to one embodiment of the present invention, the bioflocculant material can be produced and maintained in a small storage reservoir adjacent to the solar pond. Because water must periodically be added to solar ponds to replenish water lost by evaporation, the bioflocculant material can be added as a part of this make-up water. Most perferably, the bioflocculant is added to the upper layer of the pond and flocculates materials to settle them to the bottom of the pond. In this way a continuous concentration of flocculant may be achieved. This can be done at periodic intervals to maintain the water in the solar pond in top quality condition. The bioflocculant material causes the sedimentation of bentonite and other suspended particles such as kaolin, and organic materials which would otherwise lessen the clarity of the solar pond water, as well as metal ions and radioactive materials in industrial wastes. Such particles rapidly settle to the bottom of the pond, where they will not interfere with the operation of the pond.

As was noted above, flocculating activity is somewhat temperature-dependent. Since solar ponds conventionally contain salt water at temperatures between about 20° C. and 90° C., the natural efficiency of the flocculating agent is actually enhanced in the high-temperature environment of the pond.

It is to be understood that the above-described preferred embodiments are illustrative only, and other embodiments of the invention are also possible. In particular, though much emphasis has been placed on the purification of water, it is obvious that the bioflocculant of this invention could be used to purify other liquids, as well. The invention is also useful in the treatment of soils. It achieves its results by improving the colloidal properties of the soils. Thus, by adding the cellular excretions to the soil, the ability of the soil to retain moisture is improved, thus proving advantageous in irrigation.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

What is claimed is:

1. A process for clarifying a liquid containing particulates comprising treating said liquid by adding a bioflocculant excretion of a bacteria selected from the group of cyanobacteria of the Phormidium genus in a concentration sufficient of flocculate particles in the liquid.

2. The process as defined by claim 1 wherein said bacteria is species J-1 of the Phormidium genus.

3. The process as defined by claim 1, wherein said liquid is water.

4. The process as defined by claim 1, wherein said liquid is salt water.

5. The process as defined by claim 4 wherein said salt water is contained in a solar pond.

6. The process as defined by claim 5 wherein said bioflocculant is added to the solar pond with make-up water.

7. The process as defined by claim 1 comprising separating said bacteria from said bioflocculant prior to treating said liquid with said bioflocculant.

8. The process is defined by claim 1, comprising growing the bacteria in situ in said liquid, whereby bioflocculant is excreted directly into said liquid to be clarified.

9. The process as defined by claim 1 wherein said liquid is industrial waste water.

10. The process as defined by claim 1 wherein the particulate to be flocculated is selected from the group consisting of bentonite, kaolin, suspended particulates of dead sea brines, metal ions and radioactive materials in industrial wastes, and suspended particulates of turbid solar pond systems.

11. (Amended) The process as defined by claim 1, wherein the pH or said liquid is between about 4.0 and about 11.0.

12. The process as defined by claim 1 comprising providing an effective concentration of cation in said liquid to improve the flocculation of said particulates by said bioflocculant excretion.

13. The process as defined by claim 12 wherein said cation is selected from the group consisting of $Mg^{++}$, $Ca^{++}$, $Na^{+}$, or mixtures thereof.

14. The process as defined by claim 1 wherein the bioflocculant excretion is an extracellular, cell-free substance that is water-soluble, contains sugar, peptide and fatty acid moieties, is non-dialyzable, has a molecular weight greater than 100,000 based on Sephadex column elution G 150, gives a positive Anthrone test, and has an absorption peak at 205 nm. in a Perkin-Elmer spectrophotometer Model 402.

15. The process as defined by claim 1 comprising adding said bioflocculant excretion to said liquid in a concentration of between about 0.05 and 0.5 mg. per liter of said liquid.

16. The process as defined by claim 1 comprising adding said bioflocculant excretion to said liquid together with the bacteria.

17. The process as defined by claim 1 comprising growing said bacteria in situ and adjusting conditions in said liquid such that said bacteria produces an increased level of bioflocculant intracellularly and subsequently excretes the bioflocculant into said liquid.

* * * * *